US008003644B2

(12) United States Patent
Fishler

(10) Patent No.: US 8,003,644 B2
(45) Date of Patent: Aug. 23, 2011

(54) SOLID BIOCIDE FORMULATIONS

(75) Inventor: Theodor Morel Fishler, Haifa (IL)

(73) Assignee: Bromine Compounds Ltd., Beer Sheva (IL)

( * ) Notice: Subject to any disclaimer, the term of this patent is extended or adjusted under 35 U.S.C. 154(b) by 1179 days.

(21) Appl. No.: 10/552,377

(22) PCT Filed: Apr. 8, 2004

(86) PCT No.: PCT/IL2004/000317
§ 371 (c)(1), (2), (4) Date: Aug. 15, 2006

(87) PCT Pub. No.: WO2004/089081
PCT Pub. Date: Oct. 21, 2004

(65) Prior Publication Data
US 2008/0119472 A1    May 22, 2008

(30) Foreign Application Priority Data

Apr. 14, 2003  (IL) ........................................ 155435

(51) Int. Cl.
*A01N 43/66* (2006.01)
*A01N 59/14* (2006.01)
*A01N 59/06* (2006.01)
*A61K 31/53* (2006.01)
*A61K 33/22* (2006.01)
*A61K 33/06* (2006.01)
*C03B 37/018* (2006.01)

(52) U.S. Cl. ........ 514/241; 424/658; 424/659; 424/660; 424/698; 65/424

(58) Field of Classification Search ................. 514/237, 514/241; 65/424; 424/658, 659, 660, 698
See application file for complete search history.

(56) References Cited

U.S. PATENT DOCUMENTS

| 4,731,195 | A | * | 3/1988 | Olson ....................... 252/186.34 |
| 5,478,482 | A | * | 12/1995 | Jones et al. .................... 210/753 |
| 5,514,287 | A | | 5/1996 | Jones et al. |
| 5,670,059 | A | | 9/1997 | Jones et al. |
| 6,068,791 | A | | 5/2000 | Lachochi et al. |

OTHER PUBLICATIONS

International Search Report for corresponding PCT application—3 pages, (Aug. 18, 2005).

* cited by examiner

*Primary Examiner* — Sreeni Padmanabhan
*Assistant Examiner* — Sarah Pihonak
(74) *Attorney, Agent, or Firm* — Roach Brown McCarthy & Gruber, P.C.; Kevin D. McCarthy

(57) ABSTRACT

Biocidal compositions that contain biocidal components, such as an oxidant, and mixed with said components a combination of inorganic compounds capable of reducing the oxidative capacity of the biocidal components by forming a low-melting glass when heated. The biocidal composition may be heated by being ignited or subjected to a heating source, such as a fire.

18 Claims, No Drawings

SOLID BIOCIDE FORMULATIONS

FIELD OF THE INVENTION

The invention relates to new compositions of biocidals, particularly oxidants such as TCCA (trichloro-isocyanuric acid) in the form of granulates and tablets, which have reduced oxidative potential while said efficiency as biocides is not impaired in any way.

BACKGROUND OF THE INVENTION

TCCA is the basic material for a large class of household and industrial products used for treating the water of swimming pools, cooling towers, toilet bowls, detergents, paper industry, and the like. It is sold as tablets of various forms and sizes or as granulated material or powder.

TCCA is a powerful oxidant and as such its transportation and shipping is regulated by rules, varying from country to country, regarding packaging requirements. The packages should bear a warning label showing the oxidant characteristics and should be constructed so that any contact of their contents with organic or oxidizable matter is avoided. For the USA these rules are elaborated by the Department of Transportation (DOT). The packaging requirements are described in the Code of Federal Regulations (CFR), Title 49, Transportation, Parts 100-185 (Revised as of Oct. 1, 2000), §173.127(1), "Class 5, Division 5-1—Definition and Assignment of Packing Groups". The classification of packages is done according to the results of a testing procedure described by the UN Recommendations on the Transport of Dangerous Goods, Manual of Tests and Criteria, Section 34, Test O.1 "Test for Oxidizing Solids" (hereinafter, "the UN test"). To the applicant's best knowledge, prior art TCCA formulations that comply with these stringent requirements and do not require the "oxidant" labeling are not available on the market and have not been disclosed. Some formulations have been disclosed that were claimed to pass the old DOT test (hereinafter "the DOT test") for ignitability. Said test, described in Appendix F (now abandoned) to Part 173 made a comparison between the burning time of standard mixtures that used saw dust as combustible matter and a mixture of potassium bromate and potassium perchlorate as reference oxidizing material and 4:1 and 1:1 mixtures of the oxidizer to be tested with the same saw dust. Saw dust is not a well defined combustible material and contains lignin, a phenolic constituent of the wood, whose combustibility is low. This allows longer burning times of the standards and more possibility of the tested material to pass the test. However, the DOT test was abandoned and replaced with the UN test, so that the fact that a formulation passes the DOT test is not significant. The main difference between the UN test and the DOT test is that the first uses as combustible material dry, micronized cellulose fibers, well characterized by the particle size and moisture content, and uses potassium bromate alone as reference oxidant. In some cases, compositions that would not pass said test are allowed to be marketed without a warning labeling because they are limited to small packages (less than 1 kg., Package Group III).

U.S. Pat. No. 6,068,791 describes formulations containing 72-72.1% TCCA, 2.9-3.2% glycoluril, 18% Alum, 6.8% Borax and 0.1% Boric acid that are stated (but not claimed) to be able to pass the DOT test for comburancy. These mixtures contain relatively low levels of TCCA, which are not as efficient for water treatment or cleaning applications.

U.S. Pat. Nos. 5,478,482, 5,670,059 and 5,514,287 describe mixtures of 60% sodium-dichloro-s-triazinetrione (Na dichloro-isocyanurate) with 20-30% Na persulfate, 10% Na tetraborate, 0-10% aluminum sulfate and 0-20% oxone, that apparently are non-comburant by the DOT test (though this again is stated but not claimed). These compositions contain ca 36% available chlorine only, so that it could be expected that, at this level, the oxidative properties would not be significant.

It is clear, therefore, that no TCCA composition is known in the art that has high biocidal properties, and yet is non-comburant according to the UN test, is less dangerous for transport and storage than the known compositions, and does not require special labeling. It is the purpose of this invention to provide such a composition.

It is another purpose of this invention to provide such compositions that contain other oxidant biocides in general.

A further purpose is the provision of biocide tablets for the sanitation of bodies of water.

Other purposes and advantages of the invention will appear as the description proceeds.

SUMMARY OF THE INVENTION

The composition of the invention comprises mixtures of an active component that is a biocide, particularly is an oxidant and more particularly is TCCA, with a combination of inorganic compounds capable of forming a low-melting glass when heated by being ignited or subjected to a heating source, such as a fire. Preferably, the low-melting glass is formed when the composition is heated to moderately high temperatures, which may be, for instance, from 300 to 800° C. The glass covers the mixture thus decreasing its oxidant capacity. A preferred example of said combination of inorganic compounds is the combination of boron compounds and silicates. Boric acid is a suitable boric compound, but can be substituted by the same molar amounts (viz. by the same boric moiety) of borates, such as sodium tetraborate or borax. Silicates should preferably be such that their ratio $SiO_2/Na_2O$ is between 2 and 5 and should preferably have a $Na_2O$ content between 12-25 wt %, as is e.g. the case of sodium silicates (known as powdered water glass). This mixture forms, on heating, the low melting borosilicate glass that protects the biocide from contact with the surrounding, rendering it non-dangerous in case of accidental fire Preferred contents of boric acid, or amounts of boric moieties in borates, are from 2 to 15 wt % and preferably from 10 to 15 wt % of the whole composition. Preferred contents of the silicate are from 1 to 10 wt % and preferably from 2 to 8 wt % of the whole composition.

According to an embodiment of the invention, the compositions may also contain a flocculant, for example, but not only, alum (hydrated or anhydrous, sulfate of aluminum). This is desirable, for easing the removal of precipitates that may be generated in the application of the mixture.

The invention also relates to the formation of tablets, briquettes, pucks and granules based on the above compositions; and to the use of said compositions, particularly said tablets, for the sanitation of bodies of water such as swimming pools, spas, cooling towers, paper industry wastes, toilet bowls; as well as to the use of said compositions for household bleaches, and for industrial and institutional (I&I) bleaches applications, and others. The major embodiment of the present invention is a novel approach for introduction of fire-retardancy into biocide applications. It is apparent to a person skilled in the art that the active materials could be included in various multi-component compositions, for example in mixtures that include an additional algaecide.

It will be understood that the invention in its broadest aspect provides means for causing biocide compositions, having oxidant properties, less comburant, viz. less liable to enhance burning of combustible materials. Therefore it is not limited to compositions in which the main active material is TCCA but extends to compositions in which the main active material is another oxidant biocide, or a biocide that is not an oxidant. Examples of such active materials are the sodium salt of dichloro-isocyanuric acid, calcium hypochlorite, dihalo-dialkyl-hydantoins (where dihalo means dibromo-, dichloro- or bromochloro-, dialkyl means C1-C5 aliphatic hydrocarbon radical, which can be the same or different), and other halogenated isocyanurates, e.g. dichloro or monochloro acids or their salts.

DETAILED DESCRIPTION OF PREFERRED EMBODIMENTS

Examples of compositions according to embodiments of the invention wherein TCCA (trichloro-isocyanuric acid) is the biocide, the boric compound is BA (boric acid), and the silicate is SS (sodium silicate with a $SiO_2/Na_2O$ ratio of 3.22), which also comprise Alum as flocculant, are given in Table I.

TABLE I

| Mixture | Parts by weight | | | |
|---|---|---|---|---|
| # | TCCA | BA | SS | Alum |
| 1 | 90 | 8 | 5 | 10 |
| 2 | 90 | 8 | 5 | 5 |
| 3 | 90 | 8 | 2 | 10 |
| 6 | 90 | 5 | 5 | 5 |
| 7 | 90 | 5 | 2 | 10 |
| 8 | 90 | 5 | 2 | 5 |
| 9 | 80 | 8 | 5 | 10 |
| 10 | 80 | 8 | 5 | 5 |
| 12 | 80 | 8 | 2 | 5 |
| 13 | 80 | 5 | 5 | 10 |
| 15 | 80 | 5 | 2 | 10 |
| 16 | 100 | | | |

Table II presents the results of testing of the mixtures of Table I:

TABLE II

| | Burning test results | | | | | | | | | |
|---|---|---|---|---|---|---|---|---|---|---|
| Sample # | Burning | Glowing | 1/1 Smoking | Flickering | Duration | Burning | Glowing | 4/1 Smoking | Flickering | Duration |
| 1 | | | <+ | + | 3' | | | ++ | | 1' 30" |
| 2 | | | + | | 2' 25" | | | ++ | + | 1' 15" |
| 3 | | | + | + | 2' 33" | | | ++ | | 1' 35" |
| 6 | | | + | + | 1' 6" | | | ++ | + | 1' 30" |
| 7 | | | ++ | + | 2' 10" | | | ++ | | 1' |
| 8 | | | ++ | + | 1' 30" | | | ++ | | 1' 20" |
| 9 | | | + | | 3' | | | ++ | | 1' 30" |
| 10 | | | ++ | + | 3' | | | ++ | | 1' 45" |
| 12 | | | + | | 3' | | | ++ | | 1' 15" |
| 13 | | | | + | 3' | | | ++ | | 50" |
| 15 | | | + | | 3' | | | ++ | | 1' 25" |
| 16 | ++ | | ++ | | 1' | | | ++ | + | 30" |

The + indicates a positive response. More than one + indicate stronger positive responses. A comparative mixture containing only TCCA burned with flame and a lot of smoke, while mixtures 1, 2 and 7 to 12 burned only for a short time. Mixtures 6, 13 and 15 do not burn or glow. All mixtures developed smoke, some flickered but none visibly glowed.

Similar mixtures of other biocidal materials, such as halogenated dialkylhydantoins, calcium hypochlorite and the sodium salt of dichloroisocyanuric acid, taken in equivalent active halogen proportions, behaved similarly.

The anti-microbial efficacy of the exemplified compositions was tested on *E. coli* #11229, according to a modified AOAC standard method 965.13—Efficacy for Swimming Pool Disinfection. A chlorine concentration of 0.5 ppm, provided by the formulations, was enough to kill the bacteria in less than 1 minute. TCCA alone was similarly active at said concentration. This shows that the efficacy of the compositions according to the invention was not affected by the presence of the components other than the oxidant.

The compositions can be granulated by a dry or wet process. The granules can be used directly or can be further pressed into bodies, e.g. tablets or briquettes of any desired form, of convenient sizes according to the intended use.

If a soluble sanitizing agent, e.g. Na dichloro-isocyanurate (NaDCCA), is used in the formulation, the compositions can be used, as granules or bodies, for shock treatment of any body of water requiring it, due to the high solubility of the biocide.

While some embodiments of the invention have been described by way of illustration, it will be apparent that the invention can be carried into practice by persons skilled in the art with many modifications, variations and adaptations, without departing from the spirit of the invention or exceeding the scope of the claims.

The invention claimed is:

1. A fire retarded biocidal composition, consisting of more than 80 wt % of biocidal components mixed with a combination of inorganic compounds, which are capable of reducing the oxidative capacity of the biocidal components toward eventual organic or oxidizable matter, thus rendering said biocidal components non-comburant according to the UN test, by forming a glass, characterized in that said glass is formed when the composition is heated to temperatures from 300 to 800° C. by a heating source such as fire, said combination of compounds being a combination of inorganic compounds comprising boric compounds and alkaline silicates, and said inorganic compounds being in an amount to balance said biocidal components to 100 wt %.

2. Biocidal composition according to claim 1, wherein the heating source is a fire.

3. Biocidal composition according to claim 1, wherein the biocidal component is an oxidant.

4. Biocidal composition according to claim 3, wherein the oxidant is trichloroisocyanuric acid.

5. Biocidal composition according to claim 1, wherein the boric compounds are chosen from among boric acid, borax and sodium tetraborate.

6. Biocidal composition according to claim 1, wherein the silicates are sodium silicates.

7. Biocidal composition according to claim 1, wherein the silicates are sodium silicates having the ratio $SiO_2/Na_2O$ between 2 and 5 and the $Na_2O$ content between 12-25%.

8. Biocidal composition according to claim 5, wherein the contents of the boric moieties in said boric compounds, are from 2 to 15 wt % of the whole composition.

9. Biocidal composition according to claim 8, wherein said contents are from 10 to 15 wt % of the whole composition.

10. Biocidal composition according to claim 1, wherein the contents of the silicates are from 1 to 10 wt % of the composition.

11. Biocidal composition according to claim 10, wherein the contents of the silicates are from 2 to 8 wt % of the composition.

12. Biocidal composition according to claim 1, further comprising a flocculant.

13. Biocidal composition according to claim 12, wherein the flocculant is aluminum sulfate.

14. Biocidal composition according to claim 3, wherein the oxidant is chosen from the group consisting of trichloroisocyanuric acid, calcium hypochlorite, dihalo-dialkyl-hydantoins, halogenated isocyanuric acids and the salts of said acids.

15. Biocidal solid composition according to claim 1, in the form of tablets, briquettes, granules or powder.

16. Method for the sanitation of bodies of water, comprising the following steps:

(i) obtaining a fire retarded biocidal composition, consisting of more than 80 wt % of biocidal components mixed with a combination of inorganic compounds, which are capable of reducing the oxidative capacity of the biocidal components toward eventual organic or oxidizable matter, thus rendering said biocidal components non-comburant according to the UN test, by forming a glass, characterized in that said glass is formed when the composition is heated to temperatures from 300 to 800° C. by a heating source such as fire, said combination of compounds being a combination of inorganic compounds comprising boric compounds and alkaline silicates, and said inorganic compounds being in an amount to balance said biocidal components to 100 wt %, and (ii) adding said biocidal compositions to said bodies of water.

17. Method according to claim 16, wherein the bodies of water are chosen from the group consisting of swimming pools, spas, cooling towers, paper industry wastes, toilet bowls, household and I&I bleaches applications.

18. Method for rendering biocide compositions consisting of more than 80 wt % of biocidal components less comburant, which comprises mixing with the biocide a combination of inorganic compounds, which are capable of reducing the oxidative capacity of the biocidal components toward eventual organic or oxidizable matter, thus rendering said biocidal components non-comburant according to the UN test, by forming a glass characterized in that said glass is formed when the compositions are heated to temperatures from 300 to 800° C. by a heating source such as fire, said combination of compounds being a combination of inorganic compounds comprising boric compounds and alkaline silicates, and said inorganic compounds being in an amount to balance said biocidal components to 100 wt %.

* * * * *